United States Patent [19]
Plessers et al.

[11] Patent Number: 5,902,468
[45] Date of Patent: May 11, 1999

[54] DEVICE FOR CONDUCTING ELECTROCHEMICAL MEASUREMENTS IN GLASS OR SALT MELTS

[75] Inventors: Jaques Josef Plessers, Houthalen; Marc Straetemans, Eksel, both of Belgium

[73] Assignee: Heraeus Electro-Nite International N.V., Houthalen, Belgium

[21] Appl. No.: 08/872,323

[22] Filed: Jun. 10, 1997

[30] Foreign Application Priority Data

Jun. 14, 1996 [DE] Germany ............... 196 23 683
Jun. 14, 1996 [DE] Germany ............... 196 23 687

[51] Int. Cl.$^6$ ........................................ G01N 27/26
[52] U.S. Cl. ............... 204/422; 204/423; 204/435
[58] Field of Search ................. 204/412, 415, 204/421, 423, 422, 435

[56] References Cited

U.S. PATENT DOCUMENTS

| | | | |
|---|---|---|---|
| 3,449,231 | 6/1969 | Adams et al. | 204/415 |
| 3,625,026 | 12/1971 | Cocker | 65/27 |
| 3,816,269 | 6/1974 | Wilder | 204/422 |
| 4,313,799 | 2/1982 | Perkins | 204/1 T |
| 5,480,523 | 1/1996 | Cocker et al. | 204/422 |

FOREIGN PATENT DOCUMENTS

| | | |
|---|---|---|
| 2 122 758 | 9/1972 | France. |
| 30 28 270 C2 | 2/1982 | Germany. |
| 31 09 454 A1 | 9/1982 | Germany. |
| 33 03 851 A1 | 8/1983 | Germany. |
| 37 09 196 A1 | 10/1987 | Germany. |
| 38 11 865 C1 | 5/1989 | Germany. |
| 38 11 915 A1 | 10/1989 | Germany. |
| 38 11 864 C2 | 2/1990 | Germany. |
| 35 35 754 C2 | 4/1990 | Germany. |
| 2 057 695 | 4/1981 | United Kingdom. |

OTHER PUBLICATIONS

Estell, T. H., et al., "Voltametric Determination of Oxygen in Liquid Metals Using Solid Oxide Electrolytes" *J. Electrochem Soc.*, pp. 198–208 (Feb. 1972).

Hayo Müller–Simon et al. On–line determination of the iron concetration in industrial amber glass melts[1])Glastech. Ber. Glass Sci. Technol. 68 (1995) No. 9, pp. 273–277 no month available.

*Primary Examiner*—Bruce F. Bell
*Attorney, Agent, or Firm*—Panitch Schwarze Jacobs & Nadel, P.C.

[57] ABSTRACT

A device for conducting electrochemical measurements in glass or salt melts has at least one indicator electrode and one reference electrode arrangement. In order to be able to conduct very exact measurements, the tip of the indicator electrode intended to be immersed in the melt is constructed of a noble metal or noble metal alloy with at least one another noble metal, preferably iridium or an iridium alloy with other noble metals, and is mounted gas-tight in a heat-resistant tube. The indicator electrode is passed through the heat-resistant tube.

19 Claims, 3 Drawing Sheets

DEVICE FOR CONDUCTING ELECTROCHEMICAL MEASUREMENTS IN GLASS OR SALT MELTS

BACKGROUND OF THE INVENTION

The invention concerns a device for conducting electrochemical measurements in glass or salt melts with a least one indicator electrode and one reference electrode arrangement.

Such devices are widely known, especially from GB 2 057 695. Here, a measurement of the oxygen partial pressure takes place by means of an electrochemical measuring cell, also called the reference electrode arrangement, which is connected with an indicator electrode through a typical indicator and/or evaluating facility (measuring system). A platinum wire is used as the indicator electrode, which is passed through an aluminum oxide body. The platinum wire is freely exposed at the tip of the aluminum oxide body, so that it can come into contact indicator with the melt as soon as the indicator electrode dips into this. The aluminum oxide body is mounted in an aluminum oxide tube. In practice, it has become apparent that it is not possible to create a gas-tight lead-through between the platinum electrode and the aluminum oxide body. In this way, oxygen from the atmosphere above the melt penetrates to the part of the indicator electrode which stands in contact with the melt, so that the values measured there do not correspond to the actual conditions within the melt, and the measurement is thereby erroneous.

Similar measurement arrangements are known, for example, from DE 38 11 915 A1. Here too, the indicator electrode is made of platinum.

The determination of iron, sulfur or chromium in glass melts by voltametric analysis with three electrodes is known, for example, from *Glastech. Ber. Glass Sci. Technol.* 68(9), pages 273–277 (1995). Even here, the problems mentioned occur. Thus, for example, the size of the electrode surface in the glass must be known exactly.

BRIEF SUMMARY OF THE INVENTION

Proceeding from the known prior art devices, an object of the present invention is to improve the measuring accuracy of, for example, oxygen partial pressure measurements in glass or salt melts.

In accordance with the invention, the object is accomplished by the tip of the indicator electrode designed to be immersed in the melts being made of a noble metal or an alloy having two or more noble metals and being mounted gas-tight in a heat-resistant tube, whereby the indicator electrode is passed through the heat-resistant tube (out of the melt into the evaluation facility). A gas-tight mounting means that no oxygen penetrates through the tube from outside into the melt to be measured (especially a glass melt) in such an amount as to influence the measurement. The noble metal or noble metal alloy may be selected from metals of the group iridium, platinum, palladium, rhodium, or alloys of at least one of these metals with at least one further noble metal (possibly also from this group). Preferably, the noble metal or alloy thereof is iridium or an iridium alloy with at least one other noble metal. Iridium and iridium alloys have a high melting point and for this reason can be connected gas-tight with the heat-resistant tube by heat treatment. Advantageously, the heat-resistant tube can be a quartz glass tube. In the case of iridium and iridium alloys, ceramic tubes, for example of aluminum oxide, are also possible. When using a ceramic tube, it is of course necessary that the material not be an ion or electron conductor at temperatures from approximately 1000 to 1500° C.

Iridium or iridium alloys may be appropriately sintered or melted into the heat-resistant tube. Iridium has a melting point of 2447° C. It thus holds up to heating which is necessary for melting or dense sintering of aluminum oxide or for softening quartz glass. For other noble metals or noble metal alloys with lower melting points, melting of the metal tip into a quartz glass tube is appropriate.

It is conceivable to use the indicator electrodes chiefly for short-term measurements in the case of a melting into a quartz glass tube, while indicator electrodes melted or sintered into aluminum oxide tubes can also be used for long-term measurements (with so-called continuous probes).

It is expedient for the connection between the indicator electrode and heat-resistant tube on the tip of the tube destined to be immersed into the melt to be gas-tight. The tube can be open toward the rear, away from the melt. It is also expedient that the tip of the indicator electrode, which is constructed of noble metal or noble metal alloy, be connected inside the tube with a measuring wire, preferably made of molybdenum, tungsten or a chromium-nickel alloy (for example, cronix). In this way, the length of the metal wire used as an electrode can be kept short in order to save noble metal.

In the event that the measuring wire is constructed of molybdenum or tungsten, it is possible to install a metal strip of molybdenum between the tip of the indicator electrode which is constructed of noble metal or noble metal alloy and the measuring wire. The connection between noble metal and measuring wire can be melted into the heat-resistant tube. In particular, a melted-in metal strip of molybdenum assures almost perfect gas tightness.

A chromium-nickel wire cannot be melted into the heat-resistant tube without further ado, since there exists the danger that the wire will melt at the necessary temperature. The connection should therefore be arranged preferably behind the melting-in point in the tube.

It is advantageous for a high measuring accuracy that a reference electrode be arranged in a solid electrolyte capillary tube, closed on one end, which is mounted in a ceramic tube with its end facing away from the closed end through which the reference electrode is passed. It is also advantageous that the end of the reference electrode in the solid electrolyte capillary tube be surrounded by a reference material which is made of a metal-metal oxide, preferably a nickel-nickel oxide powder mixture. The reference electrode itself is suitably constructed of a chromium-nickel alloy.

It is furthermore expedient that the heat-resistant tube and the ceramic tube be filled with corundum. Furthermore, it is advantageous that the heat-resistant tube and the ceramic tube be mounted in a common carrier tube, which is preferably constructed of ceramic and which has a connection piece of usual type at its end facing away from the immersion end for mechanical coupling and for connecting indicator electrode and reference electrode with a measurement system. The carrier tube can be made of aluminum oxide and be filled with corundum spheres.

BRIEF DESCRIPTION OF THE SEVERAL VIEWS OF THE DRAWING

The foregoing summary, as well as the following detailed description of preferred embodiments of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown. In the drawings.

DETAILED DESCRIPTION OF THE INVENTION

Figure 1:
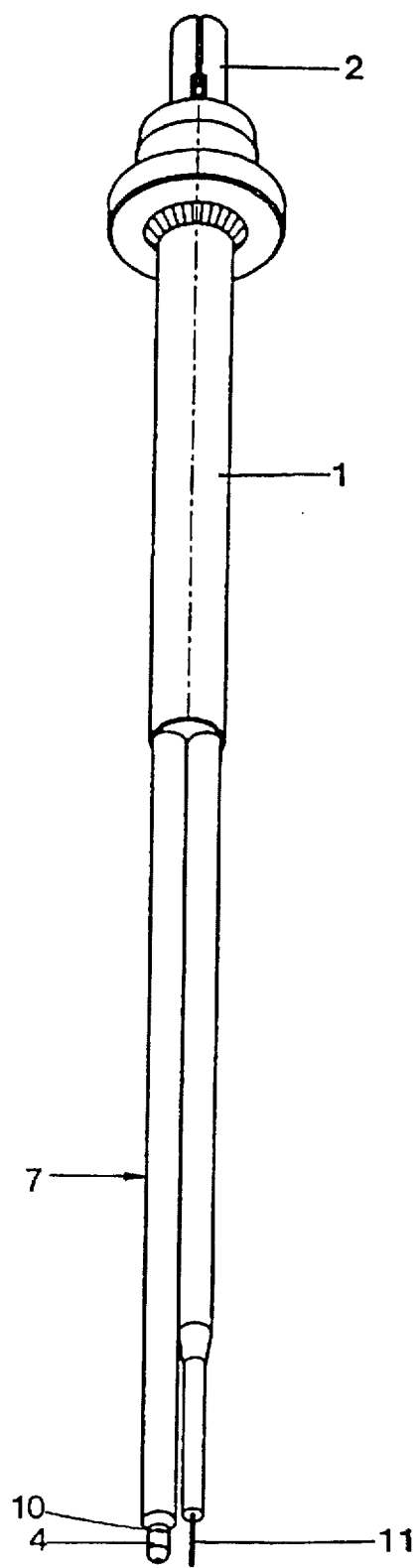
FIG. 1 shows a representation of the device of the invention.
Figure 2:
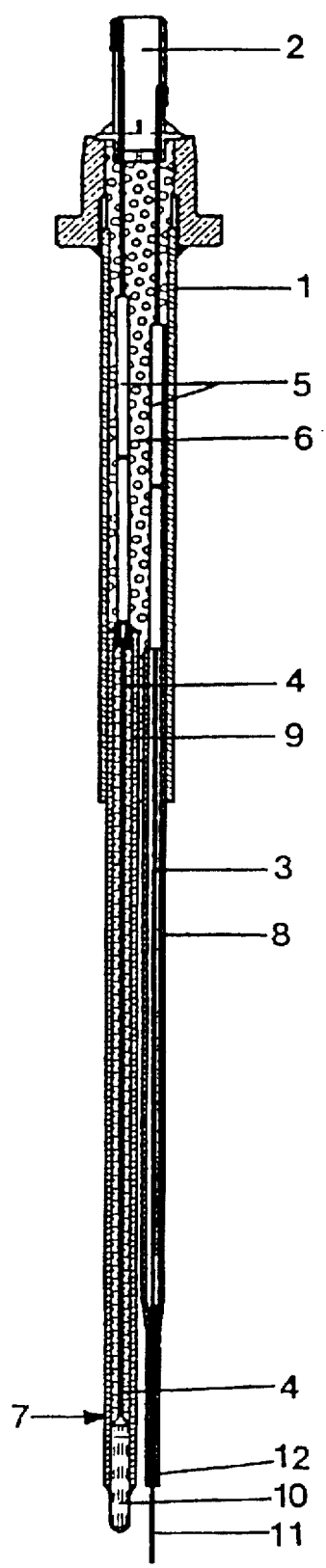
FIG. 2 is a longitudinal section through the device of the invention.

The device for measuring oxygen partial pressure, represented in FIG. 1, has a carrier tube 1 which is constructed of aluminum oxide. A connecting piece 2 is arranged on the carrier tube 1 on its end facing away from the immersion end, which is inserted into a holder (not shown in the Figure), for example a metal lance. The wires passed through the carrier tube 1, the measuring wire 3 and the reference electrode 4 are connected through connecting piece 2 with a measuring system, that means with a usual indicator and/or evaluating unit. Within the carrier tube 1, the measuring wire 3 and the reference electrode 4 are passed through quartz glass capillary tubes 5 and imbedded in spherical or ball-form corundum 6.

At the end of the device facing toward the immersion end of the carrier tube 1, the reference electrode arrangement 7 and the quartz glass tube 8, as a heat-resistant tube, are situated. The reference electrode arrangement 7 has a ceramic tube 9 of aluminum oxide, through which the reference electrode 4 is passed up to the solid electrolyte capillary tube 10. The solid electrolyte capillary tube 10 of zirconium oxide has in its interior, as reference material, a nickel-nickel oxide powder mixture, in which the reference electrode 4, which is constructed of a chromium-nickel alloy (cronix), is mounted. The indicator electrode with the measuring wire 3 is passed through the quartz glass tube 8. The tip 11 of the indicator electrode is made of iridium wire. It can, however, also be constructed of another noble metal or a noble metal alloy, preferably an alloy which predominantly contains iridium and in addition other noble metals. The tip 11 of iridium projects into the quartz glass tube 8. The tip 11 is melted in gas-tight into the end 12 of the quartz glass tube 8 along a length of about 2 cm. After this, the material of the indicator electrode changes. In order to save on relatively expensive iridium wire, the remainder of the indicator electrode is a measuring wire 3 made of cronix (chromium-nickel alloy). Instead of cronix, molybdenum or tungsten, for example, can also be used as measuring wire 3.

Figure 3:
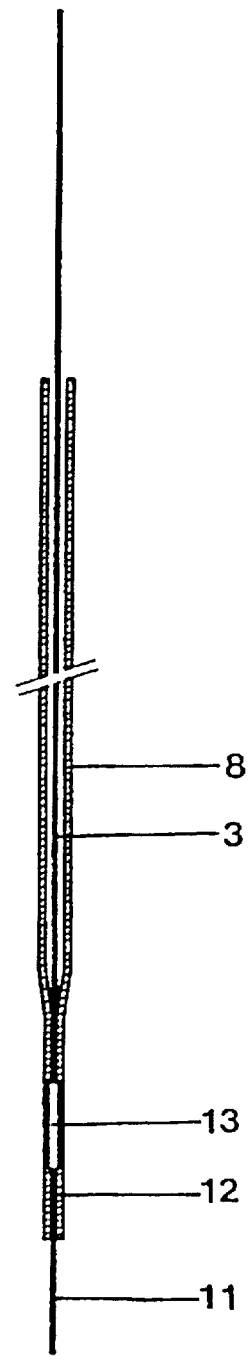
FIG. 3 is a longitudinal section through the indicator electrode melted into the heat-resistant tube.

A further possibility of constructing the indicator electrode is represented in FIG. 3. Here, the tip 11 of iridium within the quartz glass tube 8 is connected with a molybdenum strip 13, which is connected at its other end with the measuring wire 3. The measuring wire 3 can in this case, for example, be constructed of molybdenum or tungsten. The molybdenum strip 13 is, in the example depicted, completely melted into the end 12 of the quartz glass tube 8. In this way, a perfect gas tightness can be attained.

Not represented in the Figures is the possibility of leading the molybdenum strip 13 out of the melted-closed end 12 of the quartz glass tube 8 and first connecting it with the measuring wire 3 in the open tube. In such a case, cronix would also be possible as measuring wire 3.

The quartz glass tube 8 and ceramic tube 9 are provided with a corundum packing which stabilizes the position of the wires within the tubes.

Figure 4:
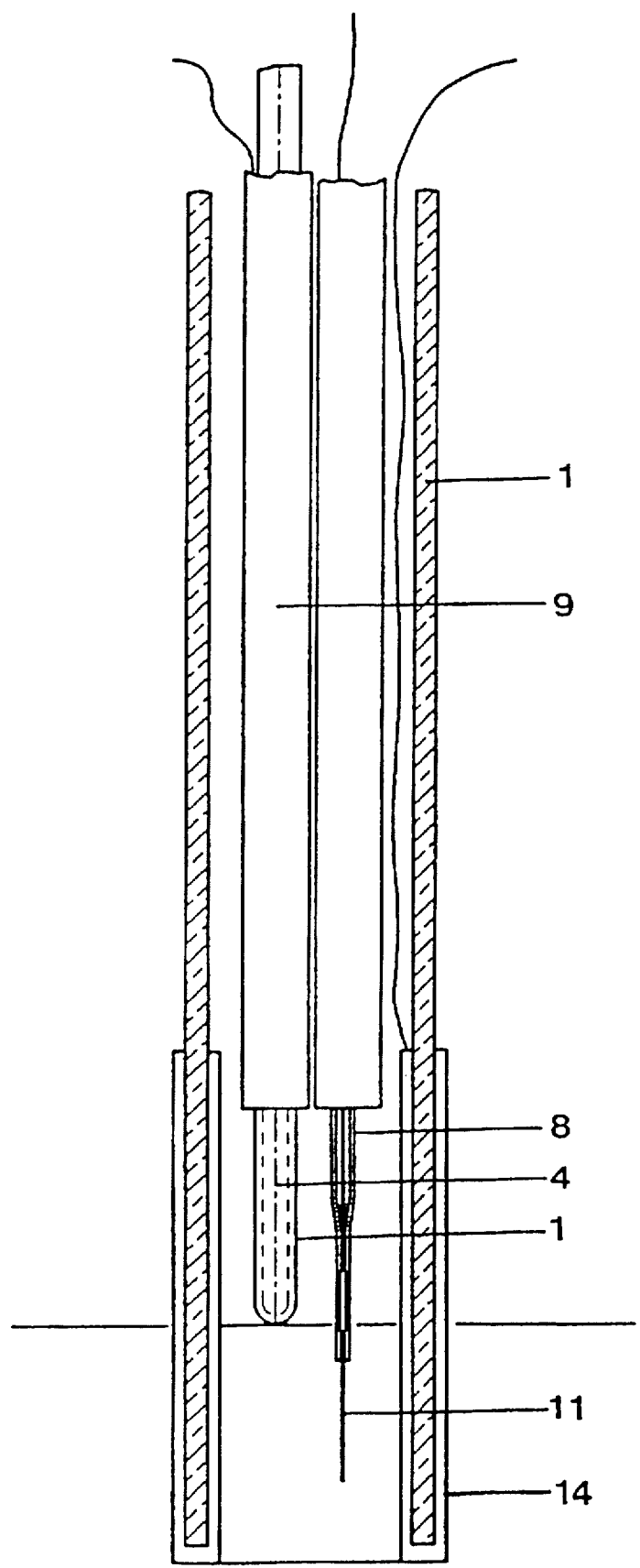
FIG. 4 is a section through a device with three electrodes.

The device represented in FIG. 4 is suited for voltametric measurement, for example, of the iron, sulfur or chromium content in a glass melt. The procedure for this is described, for example, in *Glastech. Ber. Glass Sci. Technol.* 68(9), page 273–277 (1995). In the carrier tube 1 of aluminum oxide, an indicator electrode and a reference electrode 4 are arranged. The tip 11 of the indicator electrode is constructed of iridium and melted into a quartz glass tube 8. The reference electrode 4 of platinum is arranged in a ceramic tube 9, and a counter electrode 14 of platinum is arranged on the immersion end of the carrier tube 1.

Measurement with the device described enables very reliable results, first and foremost in short-term operation. Since the device can be manufactured very economically, construction as a disposable (one use) probe is possible. When using a heat-resistant tube 8 of aluminum oxide, a long-term use is also conceivable.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

We claim:

1. A device for conducting electrochemical measurements in glass or salt melts, comprising at least one indicator electrode and one reference electrode arrangement, wherein a tip (11) of the indicator electrode intended for immersion in a melt is constructed of a noble metal or a noble metal alloy with at least one other noble metal, wherein the tip (11) is mounted gas-tight in a heat-resistant tube (8), the indicator electrode is passed through the heat-resistant tube (8) and the tip (11) of the indicator electrode extends uncovered and exposed from the gas-tight mount.

2. The device according to claim 1, wherein the heat-resistant tube (8) is a quartz glass tube.

3. The device according to claim 1, wherein the noble metal or noble metal alloy is fused to the heat-resistant tube (8).

4. The device according to claim 1, wherein the noble metal or noble metal alloy is selected from the group consisting of iridium, platinum, palladium, rhodium and alloys thereof.

5. The device according to claim 1, wherein the tip (11) is connected with a measuring wire (3) inside the heat-resistant tube (8).

6. The device according to claim 5, wherein a metal strip (13) of molybdenum is arranged between the tip (11) and the measuring wire (3).

7. The device according to claim 6, wherein the measuring wire (3) is made of molybdenum or tungsten.

8. The device according to claim 5, wherein the connection between the tip (11) and the measuring wire (3) is fused to the heat-resistant tube (8).

9. The device according to claim 5, wherein the measuring wire (3) is made of a chromium-nickel alloy.

10. The device according to claim 1, wherein the reference electrode arrangement comprises a reference electrode (4) arranged in a solid electrolyte capillary tube closed on one end, the capillary tube on its end opposite the closed end being mounted in a ceramic tube (9) through which the reference electrode (4) is passed, and wherein an end of the reference electrode (4) in the solid electrolyte capillary tube (10) is surrounded by a reference material which comprises a nickel-nickel oxide powder mixture.

11. The device according to claim 10, wherein the reference electrode (4) is made of a chromium-nickel alloy.

12. The device according to claim 10, wherein the heat-resistant tube (8) and the ceramic tube (9) are filled with spherical corundum.

13. The device according to one of claim 10, wherein the heat-resistant tube (8) and the ceramic tube (9) are mounted in a common carrier tube (1) having a connecting piece (2) on its end facing away from the immersion tip for mechanical coupling and for connecting the indicator electrode and the reference electrode and the reference electrode (4) with a measuring system.

14. The device according to claim 13, wherein the carrier tube (1) is made of aluminum oxide and it is filled with spherical corundum (6).

15. The device according to claim 13, wherein the carrier tube (1) is made of ceramic.

16. The device according to claim 1, wherein the noble metal or noble metal alloy is iridium or an iridium alloy with at least one other noble metal.

17. The device according to claim 16, wherein the heat-resistant tube (8) comprises ceramic.

18. The device according to claim 17, wherein the ceramic comprises aluminum oxide.

19. The device according to claim 17, wherein the iridium or iridium alloy is fused to the heat-resistant tube (8).

* * * * *